US009629821B2

(12) United States Patent
Puder et al.

(10) Patent No.: US 9,629,821 B2
(45) Date of Patent: *Apr. 25, 2017

(54) TREATMENT AND PREVENTION OF LIVER DISEASE ASSOCIATED WITH PARENTERAL NUTRITION (PN)

(75) Inventors: Mark Puder, Medfield, MA (US); Kathleen M. Gura, Norfolk, MA (US)

(73) Assignee: Childrens Medical Center Corporation, Boston, MA (US)

(*) Notice: Subject to any disclaimer, the term of this patent is extended or adjusted under 35 U.S.C. 154(b) by 248 days.

This patent is subject to a terminal disclaimer.

(21) Appl. No.: 12/165,785

(22) Filed: Jul. 1, 2008

(65) Prior Publication Data
US 2008/0275119 A1    Nov. 6, 2008

Related U.S. Application Data

(63) Continuation of application No. 11/267,663, filed on Nov. 4, 2005, which is a continuation of application No. PCT/US2004/037993, filed on Nov. 5, 2004.
(Continued)

(51) Int. Cl.
*A61K 31/20* (2006.01)
*A61K 31/23* (2006.01)
(Continued)

(52) U.S. Cl.
CPC .............. *A61K 31/23* (2013.01); *A23L 33/12* (2016.08); *A23L 33/40* (2016.08); *A61K 9/0029* (2013.01); *A61K 9/107* (2013.01); *A61K 31/202* (2013.01)

(58) Field of Classification Search
CPC .................................................. A61K 31/202
(Continued)

(56) References Cited

U.S. PATENT DOCUMENTS 4,820,731 A * 4/1989 Mascioli et al. .............. 514/549
5,434,183 A   7/1995 Larsson-Backstrom et al.
(Continued)

FOREIGN PATENT DOCUMENTS

EP    0311091 A1   12/1989
EP    0567653 A1    3/1993
EP    0 298 293 B1  3/1994

OTHER PUBLICATIONS

Kaufman Prevention of Parenteral nutrition-associated liver disease in children, Pediatric Transplantation 2002 vol. 6 No. 1 pp. 37-42.*
(Continued)

*Primary Examiner* — Shengjun Wang
(74) *Attorney, Agent, or Firm* — Nixon Peabody LLP

(57) ABSTRACT

The present invention is based on the discovery that parenteral nutrition (PN) induced liver disease, e.g. fatty liver disease, can be prevented and even reversed by administration of primarily omega-3-fatty acid with PN rather than the administration of the standard intravenous lipid emulsions that contain primarily plant derived omega-6 fatty acid. Thus, the present invention provides a method for treating or preventing liver disease in a human patient obtaining nutritional support through PN. The method comprises intravenous administration of an effective amount of an omega-3-fatty acid emulsion to the patient, wherein the patient is not administered phytosterols or plant derived fatty acids, e.g. omega-6 fatty acids derived from a plant source, and wherein the administration of the omega-3-fatty acid emulsion to the patient is for a period greater than three weeks. Preferably, the administration is for a period of greater than six weeks. More preferably, the administration is for a period greater than three months.

19 Claims, 7 Drawing Sheets

Related U.S. Application Data

(60) Provisional application No. 60/519,321, filed on Nov. 12, 2003.

(51) Int. Cl.
| | |
|---|---|
| *A61K 9/00* | (2006.01) |
| *A61K 9/107* | (2006.01) |
| *A61K 31/202* | (2006.01) |
| *A23L 33/00* | (2016.01) |
| *A23L 33/12* | (2016.01) |

(58) Field of Classification Search
USPC .................................. 514/560, 937, 893
See application file for complete search history.

(56) References Cited

U.S. PATENT DOCUMENTS

| 5,874,470 A | 2/1999 | Nehne et al. |
|---|---|---|
| 2003/0068385 A1 | 4/2003 | Moyer et al. |

OTHER PUBLICATIONS

Quiros-Tejeira et al., Long-Term Parenteral Nutritional Support and Intestinal Adaptation in Children with Short Bowel Syndrome: A 25-year Experience, The Journal of Pediatrics, Aug. 2004, vol. 145 pp. 157-163.*
Chen, M., et al., Int. J. of Cardiology, 36:297-304 (1992).
Chen, W.J. et al., Clinical Nutrition 15:24-28 (1996).
Van Aerde, J.E., et al., Pediatric Research, 45(2):202-208 (1999).
Chen, W., et al., Nutrition, 19:275-279 (2003).
Yeh et al., Clinical Nutrition, 15 (2): 80-83 (Apr. 1996).
Yeh et al., Nutrition, 13 (1): 32-36 (Jan. 1997).
Buchman et al., Gastroenterology, 1992, 102:1363-1370. "Lecithin Increases Plasma Free Choline and Decreases Hepatic Steatosis in Long-Term Total Parenteral Nutrition Patients.".
Buchman et al., Hepatology, 1995, 22(5):1399-1403. "Choline Deficiency: A Cause of Hepatic Steatosis During Parenteral Nutrition That Can Be Reversed with Intravenous Choline Supplementation.".
Buchman et al., Hepatology, 2006, 43(1)9-19. "Parenteral Nutrition-Associated Liver Disease and the Role for Isolated Intestine and Intestine/Liver Transplantation.".
Buchman et al., Journal of Parenteral and Enteral Nutrition, 2001, 25(5):260-267. "Choline Deficiency Causes Reversible Hepatic Abnormalities in Patients Receiving Parenteral Nutrition: Proof of a Human Choline Requirement: A Placebo-Controlled Trial.".
Cavicchi et al., Ann Intern Med., 2000, 132:525-532. "Prevalence of Liver Disease and Contributing Factors in Patients Receiving Home Parenteral Nutrition for Permanent Intestinal Failure.".
Cooke, Robert, Newsday, Jan. 23, 2007. "ALIVE, Thanks to Liver Treatment.".
Kohl et al., Journal of Pediatric Gastroenterology and Nutrition, 2007, 44:237-244. "Influence of Different Intravenous Lipid Emulsions on Hepatobiliary Dysfunction in a Rabbit Model.".
La Scala et al., Eur. J. Pediatr. Surg. 3, 1993, 224-227. "The Addition of Lipids Increases the Total Parenteral Nutrition-Associated Cholestasis in the Rat.".
Marcus, Amy Dockser, The Wall Street Journal Online, Nov. 13, 2006. "Different Rx: A Doctor's Push for Drug Pits Him Against Its Maker." Accessed Dec. 12, 2006 at 12:01am.
Roth et al., Intensive Care Med., 1996, 22:1224-1231. "Lipid deposition in Kupffer cells after parenteral fat nutrition in rats: a biochemical and ultrastructural study.".
Teitelbaum et al., Pediatrics, 2005, 115:1132-1340. "Use of Cholecystokinin-Octapeptide for the Prevention of Parenteral Nutrition-Associated Cholestasis.".
Cooke, Robert, Boston Globe, Jul. 3, 2006 edition. "How fish oil may have saved babies' lives.".
Carlson et al., Lipids, 27:901-907 (1992). "First year growth of preterm infants fed standard compared to marine oil n-3 supplemented formula.".
Chao et al., Nutrition, 16:284-288 (2000). "Effects of parenteral infusion with fish-oil or safflower-oil emulsion on hepatic lipids, plasma amino acids and inflammatory mediators in septic rats.".
Colomb et al., Journal of Parenteral and Enteral Nutrition, 24:345-350 (2000). "Role of lipid emulsions in cholestasis associated with long-term parenteral nutrition in children.".
Gura et al., Original Manuscript. "Safety and efficacy of a fish oil-based fat emulsion in the treatment of parenteral nutrition-associated liver disease.".
Illingworth et al., Arteriosclerosis, 4:270-275 (1984). "Inhibition of low density lipoprotein synthesis by dietary omega-3 fatty acids in humans.".
Nagakura et al., Eur. Respir. J., 16:861-865 (2000). "Dietary supplementation with fish oil rich in omega-3 polyunsaturated fatty acids in children with bronchial asthma.".
Manufacturer Information Sheet for OMEGAVEN®.
Quigley et al., Gastroenterology, 104:286-301 (1993). "Hepatobiliary complications of total parenteral nutrition.".
Simonpoulos, A. P., Journal of the American College of Nutrition, 21(6):495-505 (2002). "Omega-3 fatty acids in inflammation and autoimmune diseases.".
Stedman's Medical Dictionary, 27th edition, Lippincott Williams and Wilkins, 2000.
Gura et al., Original Manuscript. "Safety and efficacy of a fish oil-based fat emulsion in the treatment of parenteral nutrition-associated liver disease." published in Pediatrics Mar. 2008; 121:3 e678-e686.
Manufacturer Information Sheet for OMEGAVEN® (Aug. 1999).

* cited by examiner

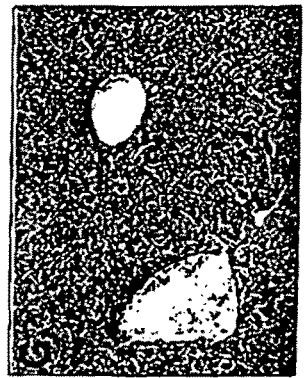
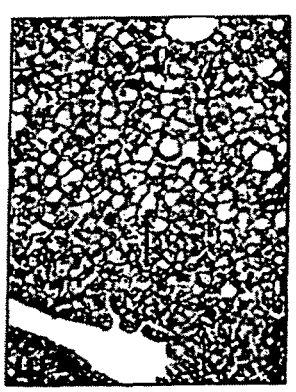
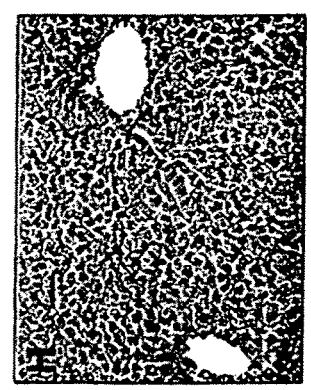
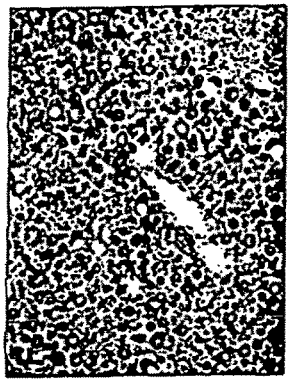
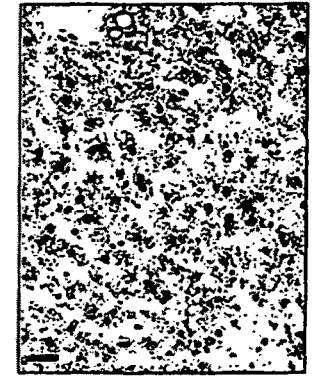

Serum liver function tests

| | Aspartate aminotransferase | Alanine aminotransferase | Alkaline Phosphatase | Total bilirubin | Direct bilirubin |
|---|---|---|---|---|---|
| Control | 72.2 ± 5.5 | 48.2 ± 3.6 | 113.2 ± 4.2 | 0.10 ± 0.02 | 0.08 ± 0.02 |
| HCD-only | 109.0 ± 6.4 § | 71.6 ± 8.2 * | 126.0 ± 5.9 | 0.20 ± 0.00 * | 0.10 ± 0.00 |
| HCD+O3FA-oral | 53.0 ± 5.8 *¶ | 23.0 ± 2.6 §¶ | 81.8 ± 7.2 §¶ | 0.13 ± 0.03 | 0.10 ± 0.00 |
| HCD+O3FA-iv | 120.0 ± 25.5 | 73.6 ± 30.8 | 129.6 ± 10.5 | 0.12 ± 0.02 † | 0.06 ± 0.02 |
| HCD+LIP-iv | 172.4 ± 66.4 | 93.4 ± 34.7 | 88.8 ± 9.4 | 0.13 ± 0.03 | 0.10 ± 0.00 |

§: $P \leq 0.01$, statistical significance compared with control animals

*: $P \leq 0.05$, statistical significance compared with control animals

¶: $P \leq 0.01$, statistical significance compared with HCD-only animals

†: $P \leq 0.05$, statistical significance compared with HCD-only animals

Data are means ± SEM n = 5 for each group

Fatty acid (triglycerides) composition of serum and liver

| Mole% | Control | HCD-only | HCD+O3FA-oral | HCD+O3FA-iv | HCD+LIP-iv |
|---|---|---|---|---|---|
| Serum | | | | | |
| 16:0 | 12.7±1.1 | 7.8±0.5 | 11.9±0.8 | 11.7±0.7 | 13.5±0.7 |
| 16:1 n-7 | 4.6±0.1 | 14.1±0.9 | 16.9±.05 | 13.4±1.1 | 9.7±0.6 |
| 18:0 | 3.0±0.2 | 2.4±0.3 | 4.0±0.8 | 3.7±0.4 | 3.0±0.3 |
| 18:1 n-9 | 20.0±1.5 | 22.9±0.5 | 26.0±0.6 | 26.9±1.1 | 26.1±0.6 |
| 18:2 n-6 | 36.8±1.2 | 9.3±0.3 | 7.0±0.5 | 9.2±1.3 | 15.9±0.2 |
| 18:3 n-3 | 0.1±0.1 | 0.0±0.0 | 0.0±0.0 | 0.0±0.0 | 1.0±0.1 |
| 20:3 n-9 | 0.2±0.0 | 10.1±0.5 | 0.8±0.2 | 0.9±0.2 | 0.8±0.1 |
| 20:3 n-6 | 0.7±0.0 | 1.3±0.1 | 0.2±0.1 | 0.6±0.1 | 1.9±0.1 |
| 20:4 n-6 | 13.0±1.2 | 24.7±1.9 * | 7.8±0.3 | 9.9±0.8 | 18.3±0.8 * |
| 20:5 n-3 | 2.8±0.1 | 0.7±0.1 | 14.2±0.8 | 10.7±1.5 | 1.0±0.1 |
| 22:5 n-6 | 0.0±0.0 | 0.3±0.0 | 0.0±0.0 | 0.0±0.0 | 0.0±0.0 |
| 22:5 n-3 | 0.4±0.0 | 0.0±0.0 | 0.6±0.0 | 0.5±0.0 | 1.6±0.2 |
| 22:6 n-3 | 5.5±0.3 | 6.4±0.4 | 10.6±0.3 | 12.6±0.6 | 7.3±0.6 |
| Liver | | | | | |
| 16:0 | 27.8±0.1 | 24.4±0.3 | 28.4±0.4 | 26.6±1.3 | 24.2±1.1 |
| 16:1 n-7 | 5.4±0.3 | 8.8±0.6 | 12.9±0.8 | 12.6±0.8 | 10.3±0.5 |
| 18:0 | 1.3±0.8 | 0.0±0.0 | 1.3±0.1 | 0.0±0.0 | 0.8±0.0 |
| 18:1 n-9 | 36.4±0.6 | 64.5±0.6 | 48.6±1.9 | 51.6±2.0 | 60.7±1.1 |
| 18:2 n-6 | 19.9±1.3 | 1.4±0.3 | 3.5±0.7 | 3.3±0.6 | 1.7±0.3 |
| 18:3 n-3 | 1.0±0.2 | 0.1±0.0 | 0.1±0.0 | 0.1±0.0 | 0.1±0.0 |
| 20:3 n-9 | 0.3±0.0 | 0.5±0.0 | 0.1±0.0 | 0.1±0.0 | 0.6±0.1 |
| 20:3 n-6 | 0.7±0.1 | 0.1±0.0 | 0.1±0.0 | 0.1±0.0 | 0.1±0.1 |
| 20:4 n-6 | 1.5±0.5 | 0.1±0.0 | 0.2±0.0 | 0.2±0.0 | 0.3±0.2 |
| 20:5 n-3 | 0.7±0.1 | 0.0±0.0 * | 0.6±0.1 | 0.5±0.1 | 0.0±0.0 * |
| 22:5 n-6 | 0.2±0.0 | 0.0±0.0 | 0.0±0.0 | 0.0±0.0 | 0.1±0.0 |
| 22:5 n-3 | 0.8±0.1 | 0.0±0.0 | 0.8±0.1 | 0.7±0.1 | 0.0±0.0 |
| 22:6 n-3 | 4.2±0.3 | 0.2±0.0 * | 3.3±0.4 | 3.9±0.4 | 0.9±0.4 * |

*: $P \leq 0.05$, statistical significance compared with control, HCD+O3FA-oral, and HCD+O3FA-iv animals

FIG. 5

COMPARISON OF PARENTERAL FAT EMULSIONS (10 GRAMS FAT/100 mL)

| Oil | Intralipid¤ (Clintec) | Liposyn II¤ (Abbott) | Omegaven¤ (Fresenius AG) |
|---|---|---|---|
| Soybean | 10 | 5 | |
| Safflower | | 5 | |
| Fish | | | 10 |
| | | | |
| % FATS | | | |
| Linoleic | 50 | 65 | 0.1-0.7 |
| α-linolenic | 9 | 4 | <0.2 |
| E.P.A. | | | 1.3-2.8 |
| D.H.A. | | | 1.4-3.1 |
| | | | |
| Glycerol | 2.3 | 2.5 | 2.5 |
| Egg Phospholipid | 1.2 | 1.2 | 1.2 |
| | | | |
| Available in United States | Yes | Yes | No |

| TEST | 09/23 (pre Omegaven) | 09/27/04 (after Omegaven Day 1 0.2 gm/kg/day) | 09/30/04 (Omegaven Day 4 0.2 gm/kg/day) | 10/4/04 (day 8 0.4 g/kg/day) | 10/7/04 (day 11 0.6 gm/kg/day) | 10/11/04 (day 15 0.8 gm/kg/day) | 10/14/04 (day 18 1 gm/kg/day) | 10/21/04 (day 25 1 gm/kg/day) | 10/27/04 (day 31 1 gm/kg/day) | 11/4/04 (day 39 1 gm/kg/day) |
|---|---|---|---|---|---|---|---|---|---|---|
| AST | 263 | 243 | 194 | 223 | 230 | 259 | 279 | 310 | 286 | 274 |
| CRP | 1.85 | | 1.21 | 1.94 | 1.28 | 2.52 | 0.71 | 0.94 | 0.61 | 0.9 |
| GGTP | 137 | | 120 | 143 | 169 | 213 | 228 | 239 | 247 | |
| Direct Bilirubin | 3.3 | 3.4 | 3 | 3 | 3.4 | 3.7 | 3 | 2.8 | 2.3 | 1.7 |
| Total Bilirubin | 4.9 | 5.2 | 4.3 | 4.4 | 4.8 | 5.5 | 4.5 | 4.4 | 3.4 | 2.5 |
| Alk Phos (110-400) | 432 | 408 | 375 (WNL) | 384 | 376 | 393 | 377 | 425 | 445 | 495 |
| ALT | 244 | 201 | 172 | 171 | 192 | 222 | 259 | 303 | 296 | 264 |

*FIG. 6*

TREATMENT AND PREVENTION OF LIVER DISEASE ASSOCIATED WITH PARENTERAL NUTRITION (PN)

CROSS-REFERENCE TO RELATED APPLICATIONS

This Application is a continuation of U.S. Ser. No. 11/267,663, filed on Nov. 4, 2005, which is a continuation of International Application No. PCT/US2004/037993, filed on Nov. 5, 2004, which designated the U.S., and which claims the benefit under 35 U.S.C §119(e) of U.S. Provisional Application Nos. 60/519,321 filed Nov. 12, 2003.

BACKGROUND OF THE INVENTION

Nutrition support through Parenteral Nutrition (PN) is necessary when patients can not be fed orally, for example when a patient has an impaired GI tract and is unable to tolerate enteral feedings.

PN is a solution that contains fluids, carbohydrates, electrolytes, proteins, amino acids, vitamins; and trace minerals. PN is administered concurrently with an intravenous lipid emulsion that provides essential fatty acids. Commercially available lipid emulsions that are currently used for parenteral use include Intralipid®(Clintec), Liposyn® and Liposyn II® (Abbott Laboratories), Travemusion® (Baxter Healthcare), and Soyacal® (Alpha Therapeutics). These lipid emulsions are composed of a vegetable oil, such as soybean oil or safflower oil, an emulsifying agent such as egg phospholipids, glycerol, and water. Thus, the fatty acid content consists of primarily of the essential omega-6 fatty acids.

The use of PN in patients of all ages has been associated with liver disease, ranging from hepatic steatosis to cirrhosis and ultimately liver failure (1-4,13-17). Investigators have proposed that it is deficiencies or toxicities of the PN solution that lead to hepatic injury (22-24) and relatively little attention has been given to idea that the lipids delivered with PN pose the problem. In fact, a leading pediatrics textbook, Principles and Practice of Pediatrics, indicates that there is little evidence to suggest that intravenous fat or glucose are associated with the liver disease hepatic cholestasis (Frank A Oski, Deangelis, C D, Feigin R D, McMillan J A, Warshaw, J B, J B lippincott Company $3^{rd}$ edition: page 1914 (Philadelphia)).

A fish oil based lipid emulsion Omegaven® (Fresenius Kabi), has been developed and used in the European market. Omegaven® is a 10% fish oil emulsion with a high percentage of omega-3 fatty acids, eicosapentaenoic acid (EPA) and docosapentaenoic acid (DHA). Simultaneous intravenous administration of Omegaven with a basic lipid emulsion such as Intralipid® provides what is believed to be an optimal ratio of omega-3 to omega-6 fatty acids. The combination of an omega-6 fatty acid lipid emulsion and a seal oil based emulsion, which is rich in omega-3 fatty acids, has also been proposed for use in PN (PCT WO 03/055323).

A study in a newborn pig model showed that intravenous administration of fish oil, which consists of primarily omega-3 fatty acids, reduced parenteral nutrition-induced cholestasis (39). However, the study was only 3 weeks in duration and long-term effects from administration of omega-3 fatty acids alone were not evaluated. In fact, the idea that one could remove an essential fatty acid from the standard regime of nutritional support by PN has not been accepted by those skilled in the art. It is believed that reduction of an essential fatty acid, such as omega-6, during a long-term therapy would clearly result in fatty acid deficiency and deterioration of the health of the patient.

PN associated liver disease is a significant drawback of parenteral nutrition. It presents a severe problem in newborns and infants who are a significant risk of developing chronic liver disease (18, 19). In addition, the prolonged use of PN in children and adults ultimately leads to non-alcoholic fatty liver disease (NAFLD). Thus, there is a need in the art to identify a means for nutritional support that does not lead to such devastating disease.

SUMMARY OF THE INVENTION

The present invention is based on the discovery that parenteral nutrition (PN) induced liver disease, e.g. fatty liver disease, can be prevented and even reversed by administration of primarily omega-3-fatty acid with PN rather than the administration of the standard intravenous lipid emulsions that contain primarily plant derived omega-6 fatty acid.

Thus, the present invention provides a method for treating or preventing liver disease in a human patient obtaining nutritional support through PN. The method comprises intravenous administration of an effective amount of an omega-3-fatty acid emulsion to the patient, wherein the patient is not administered phytosterols or plant derived fatty acids, e.g. omega-6 fatty acids derived from a plant source, and wherein the administration of the omega-3-fatty acid emulsion to the patient is for a period greater than three weeks. Preferably, the administration is for a period of greater than six weeks. More preferably, the administration is for a period greater than three months.

Any PN associated liver disease can be treated by methods of the invention. In one embodiment, the liver disease to be prevented or treated is fatty liver disease.

In one embodiment, the omega-3-fatty acid emulsion used in methods of the invention comprises fish oil. The fish oil can be derived from any fish including, but not limited to, menhaden, herring, mackerel, cod, caplin, tilapia, tuna, sardine, pacific saury, salmon, and krill.

In one embodiment, the omega-3-fatty acid emulsion used in methods of the invention is the commercially available Omegaven® (Fresenius Kabi). Alternatively, the omega-3-fatty acid emulsion can be prepared as described herein using an emulsifying agent, such as egg phosphatidylcholine, egg lecithin, L-α-dipalmitoyl phosphatidylcholine (DPPC), DL-α-dipalmitoyl phosphatidylethanolamine (DPPE), or dioleoyl phosphatidylcholine (DOPC).

The patient to be treated using the methods of the invention can be any age. For example, the patient can be a newborn, a premature newborn, an infant, a child under the age of 18, a child under the age of 12, or an adult receiving long-term nutritional support through PN.

Preferably, the omega-3-fatty acid emulsion is administered until the patient is capable of receiving adequate nutrition from enteral food intake.

In one embodiment, the omega-3-fatty acid emulsion is administered at a dose of 0.2 g/kg/day to 3.0 g/kg/day.

In another embodiment, the omega-3-fatty acid is administered at a dose of 0.5 g/kg/day to 1.0 g/kg/day.

Figure 1J:
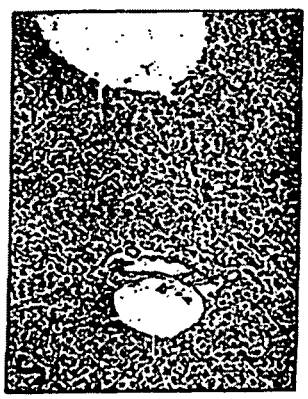
FIG. 1 shows the histology of the livers from all tested conditions. Left column H&E, middle column PAS, and right column Oil Red 0 staining as described in methods section. All sections are at 400× magnification (Bar=100
Figure 1K:
Figure 1L:
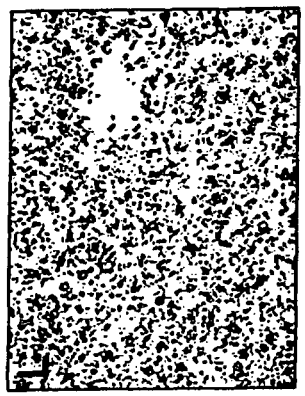
Figure 1M:
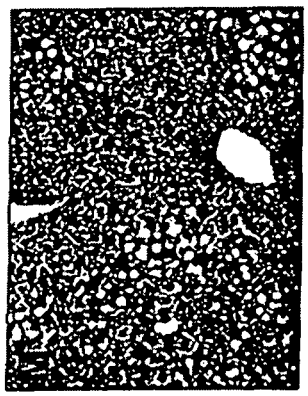
Figure 1N:
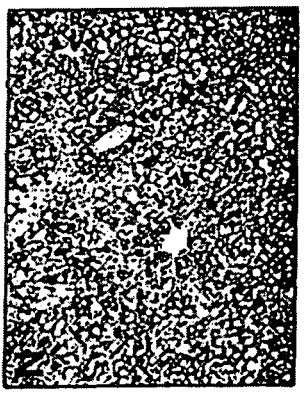
Figure 1O:
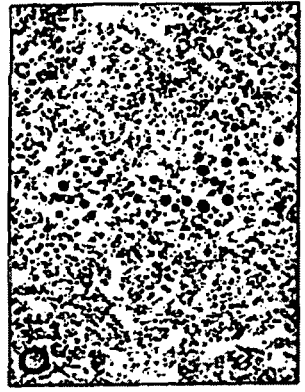

μm). Control mice show normal hepatic architecture (FIG. 1a) and glycogen storage patterns (FIG. 1b) without evidence of hepatic steatosis (FIG. 1a & FIG. 1c). Livers from HCD-only mice had diffuse macro- and micro-vesicular steatosis (arrow, FIG. 1d-FIG. 1f) with minimal glycogen storage (arrow, FIG. 1e). HCD+O3FA-oral livers had well-preserved hepatic architecture with only rare microvacuoles in the cytoplasm of midzone hepatocytes (FIG. 1g & FIG. 1i). HCD+O3FA-iv livers had minimal microvesicular steatosis in midzone hepatocytes (FIG. 1j & FIG. 1l), and appeared to have less glycogen than HCD+O3FA-oral livers (FIG. 1k). HCD+LIP-iv livers had severe macro- and micro-vesicular steatosis (FIG. 1m & FIG. 1o) with minimal glycogen storage (FIG. 1n).

Figure 2:
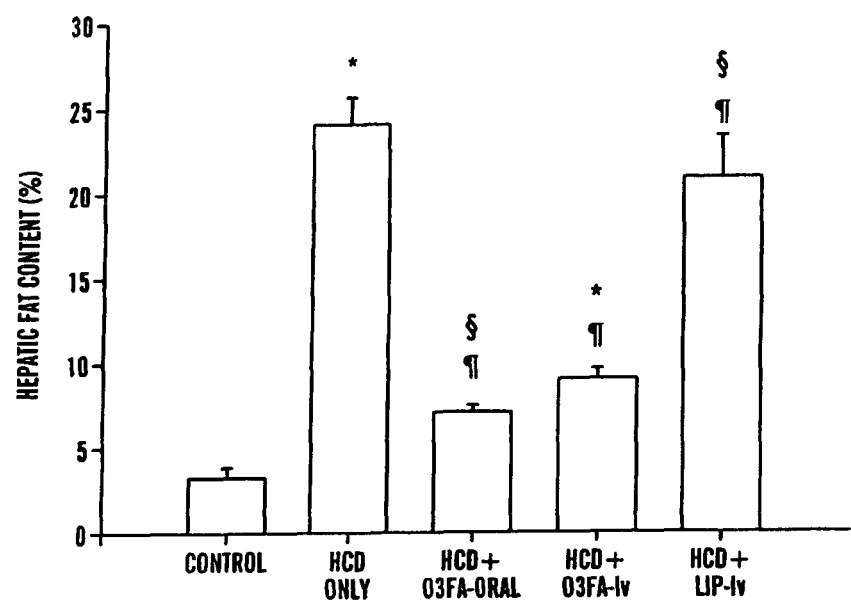

FIG. 2 shows the hepatic fat content (%) as measured by MR-spectroscopy. The liver fat content for control mice was 3.4±0.6%. Animals fed HCD-only showed an increase in liver fat content to 24.1±1.7% (*: $P \leq 0.001$). HCD+O3FA-oral and HCD+O3FA-iv mice had a liver fat content of 7.2±0.4 and 9.1±0.6%, respectively, both lower than HCD-only animals (¶: $P \leq 0.01$), but higher than control mice (§: $P \leq 0.05$ and *: $P \leq 0.001$, respectively). Hepatic fat content from HCD+LIP-iv mice was 21.0±2.5%; this was not different from HCD-only mice, but higher than control (§), O3FA-oral- and O3FA-iv-supplemented animals. Results are expressed as mean±SE (n=5 per group). (¶)

FIG. 3 shows a table indicating the results of serum liver function tests in all groups studied.

FIG. 4 shows a table indicating the fatty acid composition of serum and liver in all groups studied.

FIG. 5 shows a table that compares the composition of Intralipid® (Clintec), Liposyn II® (Abbott), and Omegaven® (Fresenius AG).

FIG. 6 shows a table indicating the levels of biochemical markers at the initiation of therapy with Omegavan® up to day 39 of therapy.

DESCRIPTION OF THE INVENTION

The present invention relates to a method for treating or preventing liver disease in patients receiving PN. The method comprises intravenous administration of an effective amount of an omega-3-fatty acid emulsion to the patient, wherein the patient is not administered phytosterols or plant derived fatty acids, e.g. omega-6 fatty acids or omega-3 fatty acids derived from a plant source, and wherein the administration of the omega-3-fatty acid emulsion to the patient is for a period greater than three weeks. Preferably, the administration is for a period of greater than 6 weeks. More preferably, the administration is for a period greater than 3 months.

In one embodiment, the liver disease to be prevented or treated is fatty liver disease. As used herein "fatty-liver disease" refers to a disease wherein fat (hepatocytes) is excessively accumulated in the liver and can cause severe diseases such as chronic hepatitis and hepatic cirrhosis. In patients with fatty liver disease, lipids, particularly neutral fat, accumulate in hepatocytes to the extent that the amount exceeds the physiologically permissible range. From a biochemical point of view, a standard for judgment of fatty liver is that the weight of neutral fat is about 10% (100 mg/g wet weight) or more of the wet weight of hepatic tissue. Fatty liver disease is generally detected by observation of elevated serum levels of liver-specific enzymes such as the transaminases ALT and AST, which serve as indices of hepatocyte injury, as well as by presentation of symptoms, which include fatigue and pain in the region of the liver, though definitive diagnosis often requires a biopsy.

In another embodiment, the disease to be treated is PN associated or induced liver disease. This disease includes both biochemical, i.e., elevated serum aminotransferase, bilirubin, and alkaline phosphatase, and histologic alterations such as steatosis, steatohepatitis, lipidosis, cholestasis, fibrosis, and cirrhosis. The disease may be progressive and worsen with the course of PN administration and appears to be more prevalent in the pediatric population. Additional risk factors for this condition include prematurity, low birth weight, long-term use, the lack of concomitant oral intake, sepsis, and multiple operative procedures. Overall, the severity of PN-induced liver pathology is thought to be inversely related to the age of the patient.

Preferred omega-3-fatty acids for use in the invention have a high content of eicosapentaenoic acid (EPA) as well as docosahexaenoic acid (DHA). The omega-3-fatty acids may be from marine or synthetic origin. For example, a suitable source of omega-3 fatty acids is fish or seal oil. Suitable fish oil sources include cod, menhaden, herring, mackerel, caplin, tilapia, tuna, sardine, pacific saury, krill, salmon, and the like.

It is known that fish oils contain eicosapentaenoic and docosahexanoic acid in the triglyceride compound which are so called highly unsaturated omega-3-fatty acids and represent essential building blocks for the human body and precursors for prostaglandins and structural elements of membrane lipid synthesis which have an important biologic role. Furthermore these acids have been considered to have an antithrombotic as well as lipid lowering effect. Since isolation of these acids from natural products and the chemical synthesis is very costly, the fish oils are considered relatively inexpensive sources of these essential fatty acids. But the use in fatty emulsions particularly for parenteral purposes mandates that these fish oils are highly purified and meet high quality standards so that with the parenteral administration no health risks and adverse reactions for the patient occur or at least can be avoided. Furthermore desirable that these highly refined fish oils are enriched with omega-3 fatty acid triglycerides. Methods of extracting and refining oils are well known in the art.

The preferred fatty emulsions are characterized by a high content of highly refined fish oil, which is highly enriched beyond the initial content of omega-3 fatty acids and their triglycerin compound as part of this specific procedure. This fish oil contains a minimum of 95 weight percent preferably a 98 weight % of monomeric triglycerides, less than 1 weight percent of oxidized triglycerides, less than 0.2 weight percent preferably less than 0.1 weight percent of trimeric and oligomeric triglycerides and less than 0.8 weight percent preferably even less than 0.5 weight percent of dimeric poly glycerides as well as less than 1.5 weight percent, preferably less than 8 weight percent of unemulsifiable particularly carbohydrates and sterane. The total content of eicosapentaenoic acid and docosahexanoic acid in the triglyceride compound is in the area of 25-50 weight percent preferably 35-50 weights percent as determined by surface percentage in the gas chromatogram. While fish oils usually have a cholesterol content of 4000 to 12000 ppm, the cholesterol content of the fish oils preferred contain less than 2500 ppm preferably less than 1500 ppm.

Preferably, the fish oil enriched omega-3 fatty acid triglyceride components contains primarily eicosapentaenoic and docosahexanoic acid. These can be present in variable ratios as determined by area percentage on gas chromatogram. These mass ratios are dependent on the nature of the fish oil and the degree of enrichment of omega-3 fatty acids. It has been shown that fish oils which contain an eicosapentaenoic acid and docosahexanoic acid in their triglyceride compound mass ratio of 0.5 to 2.6 as determined by surface area on gas chromatogram represent a fat emulsion of excellent quality and therefore this mass ratio is considered ideal and is preferred.

Fish oil is available commercially, for example 10% (wt/wt) fish oil triglycerides can be obtained from Nisshin Flour Milling Co. located in Nisshin, Japan.

To prepare the lipid emulsions in accordance with the present invention, one or more emulsifying agents are mixed with the source of omega-3 fatty acids, e.g. fish oil. Emulsifying agents for this purpose are generally phospholipids of natural, synthetic or semi-synthetic origin. A variety of suitable emulsifying agents are known in the art. Examples of suitable emulsifying agents include, but are not limited to, egg phosphatidylcholine, egg lecithin, L-α-dipalmitoyl phosphatidylcholine (DPPC), DL-α-dipalmitoyl phosphatidylethanolamine (DPPE), and dioleoyl phosphatidylcholine (DOPC). In accordance with the present invention, the total concentration of triglycerides as well as free fatty acids in the emulsifier should be low in order to minimize the contribution to the total oil concentration of the emulsion. In one embodiment of the present invention, the total concentration of triglycerides as well as free fatty acids in the emulsifier is less than about 3.5%.

In one embodiment of the present invention, lecithin is used as the emulsifying agent in the lipid emulsions. Alternatively, egg lecithin can be used as the emulsifying agent. Egg lecithin containing 80-85% phosphatidyl choline and less than about 3.5% of fat can also be used as an emulsifying agent. One skilled in the art will appreciate that other components may be present in the egg lecithin without adversely affecting the emulsifying properties. For example, the egg lecithin may contain one or more of phosphatidyl ethanol amine, lysophosphatidyl choline, lysophosphatidyl ethanolamine, sphingomeylin and other natural components.

The lipid emulsions according to the present invention typically contain between about 0.5% and about 5% (w/v) emulsifying agent. In one embodiment of the present invention, the emulsion contains between about 0.6% and about 2% (w/v) emulsifying agent. In another embodiment, the emulsion contains between about 0.8% and about 1.8% (w/v) emulsifying agent. In another embodiment, the emulsion contains between about 1.0% and about 1.5% (w/v) emulsifying agent. In another embodiment, the emulsion contains between about 1.2% (w/v) emulsifying agent.

The ratio of lecithin to source oil in the emulsion is important in determining the size of the oil globules formed within the emulsion. In one embodiment, the ratio of lecithin to source oil is between about 1:4 and about 1:20. In one embodiment of the present invention, the ratio is between about 1:4 and about 1:18. In another embodiment, the ratio is between about 1:4 and about 1:15. In another embodiment, the ratio is between about 1:4 and about 1:10.

The lipid emulsion in accordance with the present invention can further comprise additional components such as, antioxidants, chelating agents, osmolality modifiers, buffers, neutralization agents and the like that improve the stability, uniformity and/or other properties of the emulsion.

The present invention contemplates addition of one or more antioxidants to the lipid emulsion in order to help prevent the formation of undesirable oxidized fatty acids.

Suitable antioxidants that can be added to the lipid emulsions include, but are not limited to, alpha-tocopherol (vitamin E) and tocotrienols. As is known in the art, tocotrienols are a natural blend of tocotrienols and vitamin E extract concentrated from rice bran oil distillate, which have an antioxidant activity similar to that of alpha-tocopherol (vitamin E). Tocotrienols have a similar structure to vitamin E and contain three double bonds in the carbon side chain of the molecule.

When used, the concentration of antioxidant added to the emulsion is typically between about 0.002 and about 1.0% (w/v). In one embodiment, the concentration of antioxidant used in the emulsion is between about 0.02% and about 0.5% (w/v).

In one embodiment of the present invention, tocotrienols are added to the emulsion as an antioxidant. In another embodiment, about 0.5% (w/v) tocotrienols are added to the emulsion. In still another embodiment, vitamin E is added to the emulsion as an antioxidant. another embodiment, about 0.02% (w/v) vitamin E is added to the emulsion. The emulsion can further comprise a chelating agent to improve the stability of the emulsion and reduce the formation of oxidized fatty acids. Suitable chelating agents are known in the art and are those that are generally recognized as safe (GRAS) compounds. Examples include, but are not limited to, EDTA. In one embodiment of the present invention, the emulsion comprises EDTA. In another embodiment, the emulsion comprises concentrations of EDTA between about $1 \times 10^{-6}$ M and $5 \times 10^{-5}$ M.

Container design is also an important factor when manufacturing fat emulsions. If the emulsion is packaged in glass, it is preferably done in a container that is filled with nitrogen before the actual emulsion is added. After addition of the emulsion, the glass container can be filled again with nitrogen to remove dead space when the cap is affixed. Such nitrogen filling prevents peroxide formation. If the product is packaged in plastic, a DEHP free container that is gas impermeable is preferred. Preferably the container also has the appropriate overwrap to minimize peroxide formation in the lipids as well as leaching of the plasticizer from the container into the product itself. In addition, if plastic is used, it is desirable to have a desiccant in with the bag as well as an indicator that notes if there is a air leak in the overwrap. Preferably the container is also latex free.

An osmolality modifier can also be incorporated into the emulsion to adjust the osmolality of the emulsion to a value suitable for parenteral administration. Amounts and types of osmolality modifiers for use in parenteral emulsions are well-known in the art. An example of a suitable osmolality modifier is glycerol. The concentration of osmolality modifier typically ranges from about 2% to about 5% (w/v). In one embodiment of the present invention, the amount of osmolality modifier added to the emulsion is between about 2% and about 4%. In another embodiment, the amount of osmolality modifier added to the emulsion is between about 2% and about 3%. In another embodiment, about 2.25% (w/v) glycerol is added to the emulsion as an osmolality modifier. The final product should be isotonic so as to allow infusion of the emulsion through either a central or peripheral venous catheter.

One skilled in the art will understand that the pH of the emulsion can be adjusted through the use of buffers or neutralization agents. Emulsions with pH values close to physiological pH or above have been shown to be less prone to fatty acid peroxidation. One skilled in the art will appreciate that the pH of the emulsions can be adjusted through the use of an appropriate base that neutralizes the negative charge on the fatty acids, through the use of an appropriate buffer, or a combination thereof. A variety of bases and buffers are suitable for use with the emulsions of the present invention. One skilled in the art will appreciate that the addition of buffer to the emulsion will affect not only on the final pH, but also the ionic strength of the emulsion. High ionic strengths may negatively impact the zeta potential of the emulsion (i.e. the surface charge of the oil globules) and are, therefore, not desirable.

Selection of an appropriate buffer strength to provide a suitable pH and zeta potential as defined herein is considered to be within the ordinary skills of a worker in the art.

In one embodiment of the present invention, the pH of the emulsion is adjusted using sodium hydroxide. In another embodiment, the pH is adjusted with a buffer. In another embodiment, the buffer is a phosphate buffer. In another embodiment, both sodium hydroxide and a phosphate buffer are added to the emulsion.

The final pH of the emulsion is typically between about 6.0 and about 9.0. In one embodiment of the present invention, the pH of the emulsion is between about 7.0 and about 8.5. In another embodiment, the pH of emulsion is between about 7.0 and about 8.0.

The lipid emulsion can further comprise components for adjusting the stability of the emulsion, for example, amino acids or carbohydrates, such as fructose or glucose. The lipid emulsion can also be formulated to include nutrients such as glucose, amino acids, vitamins, or other parenteral nutritional supplements. The formulation of the lipid emulsion to incorporate a therapeutic agent is also considered to be within the scope of the present invention. A "therapeutic agent" as used herein refers to a physiologically or pharmacologically active substance that produces a localized or systemic effect or effects in animals and refers generally to drugs, nutritional supplements, vitamins, minerals, enzymes, hormones, proteins, polypeptides, antigens and other therapeutically or diagnostically useful compounds.

The lipid emulsions in accordance with the present invention can be prepared by a number of conventional techniques known to those skilled in the art. In general, the core lipid is first mixed with the emulsifier and the antioxidant, if one is being used.

The emulsion is then prepared by slowly adding this oil phase into water with constant agitation. If an osmolality modifier is being used, it is added to the water prior to mixture with the oil phase. The pH can be adjusted at this stage, if necessary, and the final volume adjusted with water, if required.

The size of the oil globules of the emulsion (i.e. the particle size) is an important parameter with respect to therapeutic effects and the quality of the emulsion. Since lipid particles are removed from the systemic circulation in a manner similar to chylomicrons, the size of lipid particles in the emulsion need to remain within or below the size range of the naturally occurring chylomicron, which is 0.4-1.0 um. If the particle size is larger than this, the lipid particles may be deposited in the liver, spleen and lungs resulting in significant fat load following infusion (Rahui C. M., et I al., Am. Hosp. Pharm. 1992, 49:2749-2755). Lipids with small particle sizes disperse better in the emulsion and tend to produce safer and more stable emulsions. Selection of appropriate conditions for the preparation of the emulsions according to the present invention is considered to be within the ordinary skills of a worker in the art.

The above-mentioned components can be present in various mass ratios in the fatty emulsion. The preferred form of the invented fatty emulsion contains 5-45 weight percent of highly refined omega-3 fatty acid enriched fish oil, 1-2 weight percent of emulsifier, 1-2 weight percent of emulsifier stabilizer as well as isotonizing additive, 0.02-0.02 weight percent of co-emulsifier and the rest in water. Especially preferred is a fatty emulsion with 8-35 weight percent of highly enriched omega-3 fatty acid fish oil, 1-1.5 weight percent of emulsifier, 1.5-2.5 weight percent of emulsifying stabilizer and isotonizer add on, 0.03 weight percent of co-emulsifier and the rest in water.

One procedure for manufacturing a fatty emulsion by using purified de-acidified and bleached fish oil with a content of omega-3 fatty acids includes the following: the fish oil is mixed with a fish oil compatible solvent in a weight to volume ration of fish oil to solvent of 1:1 to 1.5 is as follows. The mixture is cooled down to a temperature of −15 to −80 degrees centigrade then filtered of insoluble components, the filtrate is then cautiously separated from the solvent and the soak contained fish oils 2-4 hours steamed at 180-220 degrees Celsius. The absorption of the steamed fish oil in a nonporous solvent and filtering of the obtained solution over a selica gel—untreated with nonpolar solvent, followed by gentle removal of the nonpolar solvent and warming of the obtained highly refined fish oil enriched with omega-3 fatty acids in a nitrogen atmosphere to 50-60 degrees Celsius, filtering through a membrane filter and portion wide addition of sterane to an accurate mixture likewise kept at a controlled temperature of 50-60 degrees Celsius which contained emulsifier stabilizer and isotonization additive and co-emulsifier. Further emulsification of the formed crude emulsion at 60-70 degrees followed by filtering under nitrogen atmosphere through a membrane filter and single or multiple stepped homogenization of the emulsion at 70-85 degrees whereupon the obtained fat emulsion is cooled under nitrogen to a temperature in the range of 5-10 degrees Celsius if necessary adjusted to a pH value of 8.5-8.8 and drawn off into suitable weight under oxygen exclusion.

A preferred fatty emulsion for use in the present invention is Omegaven™ (Fresemius AG).

Methods of administering lipid emulsions to patients for PN applications or therapeutic benefit are known in the art. Typically the emulsions are administered by infusion over a suitable period of time. Appropriate dosages and administration; regimens can readily be determined by one skilled in the clinical arts.

The present invention additionally provides for kits containing the lipid emulsions for administration to a subject. The kit would provide an appropriate dosing regimen for a prescribed period.

The kits of the invention comprise one or more packages or containers containing the lipid emulsion in combination with a set of instructions, generally written instructions, relating to the use and dosage of the lipid emulsion. The kits may further comprise additional containers containing one or more nutrients or therapeutic or diagnostic compounds that may be added to the emulsion prior to administration. The packages containing the lipid emulsion may be in the form of unit doses or pharmacy bulk packages. The doses may be packaged in a format such that each dose is associated, for example, with a day of the week. There may also be associated with the kit a notice in the form prescribed by a governmental agency regulating the manufacture, use or sale of biological products, which notice reflects approval by the agency of manufacture, use or sale for human or animal administration.

The following examples are not intended to limit the present invention in any way.

EXAMPLES

Example 1

Omega-3 Fatty Acid Supplementation Prevents Hepatic Steatosis in a Murine Model of Non-Alcoholic Fatty Liver Disease Material & Methods
Animal Model Experiments were performed on 6-8 week-old C57BL6 mice (Taconic, Germantown, N.Y.). The animals, in groups of five, were housed in a barrier room and were acclimated to their environment for at least 72 hours prior to the initiation of each experiment. Animal protocols complied with the NIH Animal Research Advisory Committee guidelines and were approved by the Children's Hospital Boston Animal Care and Use Committee. The animals were weighed every third day, and at sacrifice, each group of mice consisted of 5 animals.

Diet and Experimental Groups

Experimental mice had exclusive ad libitum access to a liquid fat-free, high carbohydrate diet identical to the parenteral nutrition solution utilized at Children's Hospital, Boston. This solution contains 20% dextrose, a commercial mixture of 2% essential and nonessential amino acids (TrophAmine®, B. Braun Medical, Irvine, Calif., USA), 0.2% pediatric trace elements (American Regent, Shirley, N.Y., USA), 0.5% pediatric multivitamins (MVI Pediatric®, aaiPharrna, Wilmington, N.C.), and 30 mEq sodium, 20 mEq potassium, 15 mEq calcium (as gluconate), 10 mEq magnesium, 10 mM phosphate, 5 mEq acetate, and 30 mEq chloride per liter.

The control animals received standard rodent chow and water ad libitum. All animals in the experimental groups were fed the experimental fat free, high carbohydrate diet ad libitum placed in one bottle per cage. No additional sources of nutrition or hydration were provided for these animals. The bottles with the fat free, high carbohydrate diet were replaced daily to minimize bacterial contamination.

One group of animals received fat free, high carbohydrate diet without other supplements (HCD-only) for 19 days. A second group of animals additionally received O3FA as a commercial lipid emulsion (Omegaven™, Fresenius Kabi Deutschland GmbH, Neufahrn, Germany) via orogastric gavage at 600 µl every other day (HCD+O3FA-oral). This dose (2.4 g of fat/kg body weight of fish oil) contains 7.5-16.9 mg of omega-3 eicosapentaenoic acid (EPA) and 8.6-18.5 mg of omega-3 docosahexaenoic acid (DHA). A third group of animals was similar to HCD+O3FA-oral but received the same dose of O3FA intravenously (HCD+O3FA-iv). A final group of animals (HCD+LIP-iv) received fat free, high carbohydrate diet for 19 days supplemented by 600 µl every other day (4.8 g of fat/kg body weight) of a standard intravenous lipid emulsion (20% Intralipid®, Baxter Healthcare/Fresenius Kabi Clayton LP, Clayton, N.C., USA).

Specimen Collection

At 19 days, mice were anesthetized with 300 µl of 2.5% Avertin (Tribromoethanol, Sigma-Aldrich Corporation, St. Louis, Mo.) by intraperitoneal injection. Approximately 400 µl of blood was collected from each mouse via retro-orbital puncture. The specimens were then placed into serum separator tubes (Becton Dickinson, Franklin Lakes, N.J.), and centrifuged at 4° C. at 8000 rpm for 10 minutes to collect serum. Serum was frozen at −80° C. and delivered to the Clinical Laboratory at Children's Hospital for measurement of aspartate aminotransferase, alanine aminotransferase, alkaline phosphatase, and total and direct bilirubin levels. A fatty acid profile was also obtained from these samples as described below.

Animals underwent a midline laparotomy to observe, excise, and weigh the liver. Approximately one half of the liver was fixed in 10% formalin overnight, washed with phosphate buffered saline, and then embedded in paraffin. After cutting 5 µm sections, slides were stained at the Harvard Rodent Pathology Facility and the Department of Pathology, Children's Hospital Boston with H&E to examine cellular architecture and lipid accumulation, and with Periodic Acid-Schiff (PAS) to identify the presence of glycogen.

Another portion of the liver was collected as frozen sections, placed in embedding medium (Optimal Cutting Temperature OCT, Sakura Fenetek, Torrance, Calif.), and promptly immersed in liquid nitrogen. A last portion was immediately snap frozen in liquid nitrogen and placed on dry ice for future fatty acid analysis. The samples were stored at −80° C. Sections were stained at the Harvard Rodent Pathology Facility and the Department of Pathology, Children's Hospital Boston with Oil Red 'O' to visualize hepatic fat.

Magnetic Resonance Imaging.

The remaining liver was snap frozen and stored at −80° C. for evaluation by magnetic resonance (MR) spectroscopy to determine percentage liver fat content. MR imaging and spectroscopy were performed on a Bruker 8.5 T magnet. The liver samples were thawed at room temperature 1 hour prior to the MR analyses. Spin-lattice relaxation time T1 measurements were made with the saturation recovery approach using spin echo images with a TE of 6.4 milliseconds and 8 TR's ranging from 0.05-4000 msec. Three 2 mm thick slices were imaged for each sample and the saturation recovery curves were generated from signal intensities measured in identically sized regions of interest within a given slice. Care was taken to exclude macroscopic fat from the selected region of interest. Free induction decays with 1024 time points and a 5 kHz bandwidth were also acquired from each sample using a hard 90° radiofrequency pulse with 16 signal averages, a 10 s TR, and a flip angle of 90°. Spectra were obtained following Fourier transformation and phasing, and percent fat content was determined relative to water by numerical integration of the areas under the lipid and water peaks by an independent blinded reviewer.

Fatty Acid Analysis

Each serum sample (45 µl) was diluted to 0.5 ml in phosphate buffered saline before lipids were extracted with 6 volumes of chloroform-methanol (2:1, v/v), centrifuged at 800×g for 3 min, and the resulting lower phase aspirated. Heptadecanoic acid was added to all samples as an internal standard in the form of triheptadecanoyl glycerol and diheptadecanoyl phosphatidylcholine (30 µg of each, from chloroform:methanol (1:1, v/v) stock solutions) (Nu-Chek Prep, Elysian, Minn.) prior to extraction. Lipid extracts from the different sample preparations were fractionated into triglycerides and phospholipids by solid phase chromatography using an aminopropyl column, as described elsewhere (46). The resulting fractions were evaporated to dryness under nitrogen. Fatty acids were transmethylated by alkaline methanolysis using the $BF_3$ reagent kit (Supelco, Bellefonte, Pa.). Dry fractions were resuspended in 0.5 mL of methanolic-base and incubated at 100° C. for 3 min, followed by addition of boron trifluoride-methanol (0.5 mL), incubation at 100° C. for 1 min, addition of hexane (0.5 mL), incubation at 100° C. for 1 min, and addition of 6.5 mL of saturated NaCl. Samples were centrifuged at 800 g for 4 min. The hexane upper layer was transferred to a new glass tube and an aliquot injected in a Hewlett Packard 5890A gas chromatograph. A Supelcowax column of 30 m length and 0.5 mm internal diameter was used. Initial temperature was 150° C. and final temperature 260° C. FID temperature was 300° C. and the total running time 27 min. Fatty acid methyl ester peaks were identified by comparison of retention times of standard mixtures (Nu-Chek-Prep, Elysian, Minn.), and quantified in comparison with the internal standard (methylheptadecanoate) detector response. Mouse livers were homogenized in PBS by sonication and the lipid fraction extracted by addition of six volumes of chloroform-methanol (2:1, v/v). The subsequent processing for fatty acid profiling was performed as for blood serum.

Statistical Analysis

Comparisons of means between two experimental groups were made using two-tailed, independent t-tests. Comparisons between multiple experimental groups were performed using a one-tailed, ANOVA test. $P<0.05$ was considered statistically significant. All statistical tests were performed using SigmaStat (SPSS, Chicago, Ill.). Values are listed as mean±standard error of the mean (SEM).

Results

Animal and Macroscopic Liver Findings

All animals survived the protocol, and no animal had any signs of morbidity. All experimental groups gained weight on the fat free, high carbohydrate diet after 19 days (data not shown). There were no statistically significant differences in animal weights among experimental groups.

At sacrifice, livers from the groups supplemented with O3FA (intravenous and oral) had a similar macroscopic appearance as those of the control animals. Livers from HCD-only and HCD+LIP-iv, however, were pale yellow, suggesting fatty liver changes. There were no significant differences in liver weights between groups (data not shown).

Histology

A pathologist blinded to the groups performed histological evaluation of the livers. There were no signs of steatohepatitis, as we did not observe any acute inflammatory changes in the experimental groups on H&E sections.

FIG. 1 presents histologic results from all groups. Control mice (chow-fed) showed normal hepatic architecture (FIG. 1a) and glycogen storage patterns (FIG. 1b), without evidence of hepatic steatosis (FIGS. 1a-1c). In contrast, livers from HCD-only mice had diffuse macro- and micro-vesicular steatosis. These changes were most marked (black arrow) in the peri-portal and midzone hepatocytes (FIGS. 1d-1f). Central vein hepatocytes were spared of steatosis for a 2-3 cell layer, cells outside this perimeter, however, showed an abrupt change to steatosis (red arrow). HCD-only livers revealed minimal PAS-positivity in these sections, indicating minor glycogen storage (FIG. 1e). Most of the PAS-positive cells were present in a 2-3 cell layer around the central vein (green arrow). HCD+O3FA-oral livers had well-preserved hepatic architecture with only rare microvacuoles in the cytoplasm of midzone hepatocytes (FIGS. 1g and 1i). PAS staining was strongly positive, finely granular, and diffuse but most prominent within hepatocytes around the portal and central vein regions, and less prominent in the mid zone (FIG. 1h). HCD+O3FA-iv livers had minimal microvesicular steatosis in midzone hepatocytes (FIG. 1j-1l), and there was positive PAS staining (FIG. 1k) albeit to a lesser extent than HCD+O3FA-oral livers. HCD+LIP-iv livers had severe macro- and micro-vesicular steatosis (FIGS. 1m-1o) that, in contrast to HCD-only livers, included the central vein hepatocytes with minimal glycogen storage.

Serum Liver Function Tests

Serum liver function tests were obtained as an additional marker of liver injury. The results for these tests are summarized in FIG. 3. Values obtained from control chow-fed mice were considered to be within the normal range. The levels of aspartate aminotransferase, alanine aminotransferase, and total bilirubin were significantly higher in the HCD-only animals (109.0±6.4 U/l, 71.6±8.2 U/l, and 0.20±0.00 mg/dl, respectively) compared with controls (72.2±5.5 U/l (P≤0.01), 48.2±3.6 U/l (P≤0.05), and 0.10±0.02 mg/dl (P≤0.05), respectively). Interestingly, both aspartate aminotransferase (53.0±5.8 U/l) and alanine aminotransferase (23.0±2.6 U/l) values in the HCD+O3FA-oral treated animals were significantly lower than control animals (P≤0.05 and P≤0.01, respectively) and HCD-only animals (P≤0.01). In addition, alkaline phosphatase levels were significantly decreased in the HCD+O3FA-oral (81.8±7.2 U/l) mice compared with control animals (113.2±4.2 U/l, P≤0.01) and HCD-only animals (126.0±5.9 U/l, P≤0.01). The serum liver function tests of the HCD+O3FA-iv or HCD+LIP-iv animals were not different from control animals or HCD-only animals except for total bilirubin levels of HCD+O3FA-iv animals (0.12±0.02 mg/dl). These were significantly lower than HCD-only mice (P≤0.05).

Radiological Fat Measurements

In order to quantify changes in hepatic fat content, livers were studied with MR spectroscopy. Livers of control mice receiving only chow were used as a baseline to which all groups were compared. There was a close correlation between the percent fat calculated from the MR spectroscopy data and degree of T1 shortening determined from the T1 relaxation curves (data not shown). Liver fat content values for all experimental groups are demonstrated in FIG. 2.

The liver fat content for control mice was 3.4±0.6%. Animals fed HCD-only showed a significant increase in liver fat content to 24.1±1.7% (P≤0.001). HCD+O3FA-oral and HCD+O3FA-iv mice had a liver fat content of 7.2±0.4 and 9.2±0.6%, respectively. These values are all significantly lower than HCD-only animals (P≤0.01), but significantly higher than control mice (P≤0.05 and P≤0.001, respectively). Livers from HCD+LIP-iv mice had a fat content of 21.0±2.5%; this was not different from HCD-only mice, but significantly higher than control animals (P≤0.05), and O3FA-oral- and O3FA-iv-supplemented animals (P≤0.01).

Fatty Acid Analysis

A comprehensive analysis of fatty acid composition of serum and livers was performed; the results are summarized in FIG. 4. As expected, animals fed HCD-only were essential fatty acid deficient, whereas all other animals, including HCD+LIP-iv, were not. Essential fatty acid deficiency is generally characterized as a serum Mead acid (20:3 n-9) to arachidonic acid (20:4 n-6) serum triglyceride ratio (MA:AA) greater than 0.2. The MA:AA for HCD-only was 0.43±0.06, while the ratios for the animals receiving standard rodent chow, HCD+O3FA-oral, HCD+O3FA-iv, and HCD+LIP-iv were 0.01±0.00, 0.02±0.01, and 0.10±0.02, respectively. These ratios were also demonstrated in the liver tissue fat of the studied animals (FIG. 4). Animals receiving HCD-only also demonstrated a significant amount of de novo lipogenesis as indicated by high absolute amounts of liver palmitate (16:0), palmitoleate (16:1 n-7), and oleate (18:1 n-9), compared with control animals (36.3±2.1, 12.7±0.5, and 85.8±4.3 nmoles/μl versus 4.6±0.6, 0.9±0.1, and 6.1±0.7 nmoles/μl, respectively)(P≤0.001). The total liver fat content of HCD-only fed livers as determined by fatty acid analysis was also significantly higher than control animals (137.9±5.5 versus 16.7±2.1 nmoles/mg, P≤0.001). As expected, the molar percentage of the O3FA eicosapentaenoic acid (20:5 n-3) and docosahexaenoic acid (22:6 n-3) in the livers of control (0.7±0.1 and 4.2±0.3, respectively), HCD+O3FA-oral (0.6±0.1 and 3.3±0.4, respectively) and HCD+O3FA-iv (0.5±0.1 and 3.9±0.4, respectively) animals are similar, whereas the percentages in the HCD-only (0.0±0.0 and 0.2±0.0, respectively) and HCD-LIP-iv (0.0±0.0 and 0.9±0.4, respectively) are significantly lower (P≤0.05). Interestingly, the relative amounts of serum arachidonic acid in these groups were significantly higher than in the control and O3FA-supplemented animals (P≤0.05) suggesting a potential for a greater degree of inflammation.

Discussion

We show that supplementation of O3FA can prevent the occurrence of dietary-induced hepatic steatosis in a murine model of parenteral nutrition. This model results in severe steatotic damage to the liver within 19 days and is accompanied by essential fatty acid deficiency and enhanced de novo lipogenesis (45). The liver injury that is observed in this model is essentially identical to that seen in conventional rodent models that utilize intravenous parenteral nutrition. However, this model is unique in that it is easy to manage and, since there are no intravenous catheters present, interpretation of data is not confounded by catheter sepsis seen in other models dependent on intravenous access where parenteral nutrition can only reliably be administered for 7 days (47, 48). Furthermore, this model enables us to specifically study the roles of lipid solutions in parenteral nutrition-induced hepatic steatosis and allows for potential use of genetically modified animals to examine specific molecular mechanisms of such injury. The caloric intake of mice on this regimen is sufficient to satisfy established dietary energy needs. We emphasize that the amount of lipid that was supplemented, either as O3FA or as Intralipid®, did not affect satiety in these animals as the daily per animal intake of the fat free, high carbohydrate diet averaged 15 ml for all experimental groups; this corresponded to approximately 450 kilocalories/kg/day, a caloric load similar to the established dietary energy needs of the mouse (49). Furthermore, because all animals gained appropriate weight compared with control animals, it appears that the supplemented lipids did not contribute substantially to the total caloric intake in these animals.

Our results demonstrate that O3FA supplementation, both orally and intravenously, but not intravenous supplementation of a standard lipid emulsion, can attenuate hepatic steatosis in mice. It has been well described that essential fatty acid deficiency alone can cause fatty changes of the liver (50) and that reversing essential fatty acid deficiency can prevent hepatic steatosis (51). Although our model produces essential fatty acid deficiency, we have shown that the beneficial effect of O3FA supplementation has on hepatic steatosis is not solely due to the reversal of essential fatty acid deficiency in these mice, which both routes of administration of O3FA were able to accomplish through their small but important content of arachidonic acid. In this study we demonstrate that animals receiving the fat free, high carbohydrate diet supplemented with a standard intravenous lipid emulsion (HCD+LIP-iv group) develop severe hepatic steatosis, similar to HCD-only as demonstrated by histology, MRI liver fat content data, and liver function tests. These animals are, however, not essential fatty acid deficient, since they are provided with substantial quantities of the essential fatty acid, linoleic. In contrast, animals receiving the fat free, high carbohydrate diet supplemented by intravenous O3FA, and also those supplemented through the orogastric route, do not develop fatty changes of the liver. These data suggest that the content or perhaps the ratio of omega-6:omega-3 fatty acids, and not the essential fatty acid status is paramount in preventing hepatic steatosis in this model. It has been shown that a high polyunsaturated omega-6:omega-3 long chain fatty acid ratio is associated with non-alcoholic fatty liver disease and may favor lipid synthesis over oxidation and secretion (43). The standard lipid emulsion we administered had a 15 times higher polyunsaturated omega-6:omega-3 fatty acid ratio compared with the O3FA emulsion and 11 times higher than the normal chow (data not shown).

In conclusion, we have demonstrated that enteral and intravenous supplementation of O3FA can ameliorate hepatic steatosis in a murine model of parenteral nutrition as demonstrated by histology, MR spectroscopy, serum liver function tests, and serum and liver fatty acid analysis. In contrast, supplementation with the standard intravenous lipid emulsion Intralipid® does not improve the fatty liver changes in these animals.

Example II

Parenteral Fish Oil Reverses Parenteral Nutrition Associated Liver Disease in an Infant We describe an infant with parenteral nutrition (PN) associated liver disease whose disease progression was halted upon the discontinuation of conventional intravenous fat emulsions and with the initiation of therapy using a parenteral fat emulsion consisting solely of fish oils rich in omega-3 fatty acids. Case Report A 5.5-month-old infant boy is described. He was born prematurely at 34 weeks and was noted to have intrauterine gastroschisis and volvulus. At exploration, he was found to have a dilated duodenum with approximately 20 cm of small bowel, and matted small bowel that of questionable viability. He underwent a serial transverse enterplasty procedure (STEP) that lengthened the duodenum to approximately 52 cm. A duodenostomy was placed. The remainder of the small and large bowel were left intact in the pelvis. Since birth, he has been maintained on PN despite numerous attempts to initiate enteral feedings. A liver biopsy done at one month of age showed mild predominantly centrilobular, hepatocellular damage with ballooning, cholestasis, local steatosis and focal giant cell transformation, expansion of portal tracks with mild inflammation, bile duct proliferation, and mild fibrosis, mild periportal iron deposits. He had progressed to bridging fibrosis as reported on his most recent biopsy by four months of age. These aforementioned changes are consistent with PN cholestasis that can lead to fulminate hepatic failure requiring a liver transplant if PN therapy is unable to be discontinued. He was listed for a liver/small bowel transplant at five months old. He has hepatosplenomegaly, with his liver edge 4 cm below his right costal margin.

Since day of life 1, he received parenteral lipid emulsions composed of soybean oils. Lipids are necessary in PN dependent patients because of their high caloric value and essential fatty acid content, they have been implicated in predisposing patients to PN associated liver disease because of their phytosterol content. An alternative product not containing phytosterols was initiated that is comprised solely of fish oils (Omegaven™), Fresenius Kabi A G, Bad Homburg v.d.h, Germany) (FIG. 5). This product is not approved for use in the United States therefore informed consent, institutional review board (IRB) and FDA emergency approval were obtained. Omegaven™ treatment was initiated at a dose of 0.2 g/kg/day IV and advanced to 1 g/kg/day over a 14-day period. As part of the treatment protocol. Additional non-protein calories were provided as carbohydrates. No other parenteral form of fat emulsion was administered during Omegaven™ therapy. The same standards of care provided to all patients receiving parenteral nutrition solution were followed.

Omegaven™ was started at 5 months of age. His weight was 7.18 kg ($25^{th}$-$50^{th}$ percentile), length 61 cm ($3^{rd}$ percentile), and head circumference 42 cm (10th-25th percentile). All were plotted on the NCHS growth chart for a corrected age of 5½ months. His left arm anthropometrics show mid-arm circumference is 15.5 cm (approximately $50^{th}$ percentile), triceps skin folds 7.5 mm ($15^{th}$-$50^{th}$ percentile), and mid-arm muscle area 16.8 $cm^2$ ($95^{th}$ percentile).

His parenteral nutrition formulation consists of 15% dextrose and 2% amino acids that is infused over 11 hours each night. He also receives Omegaven at 1 gm/kg/day infused over 11 hours. This provides 85 kcals/kg/day and 2.5 grains of protein/kg/day. He receives breast milk 15 mL/hour for 24 hours via nasoduodenal tube. This provides an additional 29 kcals/kg/day. His total intake from the breast milk, PN and Omegaven is 114 calories/kg, 2.9 g of protein/kg with approximately 25% via the enteral route.

To improve his gut motility he receives erythromycin 9 mg/kg/day, metoclopramide 0.6 mg/kg/day, and pantoprazole 2.8 mg/kg/day day administered enterally via nasoduodenal tube. His parenteral nutrition solution also contained famotidine 1 mg/kg/day. As a part of routine management of patients with parenteral nutrition associated cholestasis, he received ursodiol 20 mg/kg/day via the nasoduodenal tube.

His biochemical markers at the initiation of therapy with Omegaven are listed in FIG. 6. Initially, he experienced a dramatic decline in hepatic enzyme levels, although they subsequently increased in conjunction with receiving a series of childhood immunizations. Once he was able to achieve his goal dose of Omegaven, his direct bilirubin declined.

Discussion

Although the pathological features of PN-induced liver injury have been well described, the etiology, prevention, and treatment of this disease are not well understood. Multiple hypotheses exist to explain the pathogenesis of PN-induced liver injury including altered gut hormonal profiles, the propensity for bacterial translocation in the absence of enteral intake, intestinal stasis resulting in the reduced clearance of hepatotoxic bile acids, and direct deficiencies or toxic components of the PN solution itself resulting in excessive glucose calorie uptake, excessive lipid infusion, or nutritional deficiencies such as essential fatty acid deficiency. None of these theories has been demonstrated consistently, and it is currently thought that the etiology of PN-associated hepatotoxicity is multifactorial. Available treatment for this disease process is limited and has achieved moderate success at best. Care of the PN-dependent patient is focused on gradually increasing enteral caloric provisions while the residual bowel adapts to its primary pathology so that PN use may be discontinued. In fact, it has been shown both experimentally and clinically that partial enteral nutrition, when tolerated, helps to protect against development of PN-associated liver injury. In severe cases of refractory hepatic failure, liver transplantation with or without accompanying small bowel transplantation remains the only treatment option.

Recent evidence has demonstrated that lipids are metabolized differently depending on their route of administration. Enteral lipids are absorbed by the enterocyte in the form of a micelle and packaged into chylomicrons for ultimate disposal in the liver. Once in the bloodstream, these particles rapidly acquire apolipoproteins from circulating high-density lipoproteins and can subsequently be metabolized by the liver. The emulsified particles of commercially made and intravenously administered lipid emulsions, such as Intralipid®, mimic the size and structure of chylomicrons, but differ in their content. In contrast to chylomicrons, artificial lipid particles primarily contain essential fatty acids and omega-6 triglycerides and are devoid of cholesterol or protein. Other studies have suggested that these omega-6 fatty acid-containing emulsions are dependent on lipoprotein lipase, apolipoprotein E, and low-density lipoprotein receptors for clearance, and are metabolized with less lipolysis and release of essential fatty acids than chylomicrons. In fact, it appears that they may be cleared as whole particles by tissues other than the liver.

The mechanism of clearance of omega-3 fatty acid containing lipid emulsions is unknown but appears to be largely independent of the pathways identified above. Furthermore, omega-3 fatty acid solutions have been shown to decrease de novo lipogenesis, prevent or attenuate PN-induced hepatosteatosis in rats and guinea pigs and ameliorate the severity of high-fat diet-induced hepatosteatosis in rats. In addition, omega-3 fatty acids can interfere with the arachadonic acid pathway of inflammation. They can displace arachadonic acid from tissue fatty acid pools, thereby reducing the availability for eicasanoid-synthesizing enzymes and inflammation.

Omega-3 fatty acid emulsions are beneficial in the prevention of steatotic liver injury possibly through inhibition of de novo lipogenesis, the reduction of arachadonic acid-derived inflammatory mediators, prevention of essential fatty acid deficiency through the presence of small amounts of arachadonic acid, and improved clearance of lipids from the serum.

At present, there is only one soy-free emulsion formulation available, Omegaven™. This is a fish oil emulsion that consists primarily of omega-3 fatty acids. Like soy-containing formulations, Omegaven™ contains egg phospholipids and glycerol. Unlike the soy-containing formulations, it is not indicated as a sole source of fat calories, but rather as a supplement for patients receiving parenteral nutrition whose underlying disease may benefit from an increased intake of omega-3 fatty acids. It is thought that appropriate intake of omega-3 fatty acids would improve immunological resistance and offer some protection against inflammatory tissue damage and capillary permeability. Supplementation is not recommended for more than 4 weeks and is contraindicated in patients with impaired lipid metabolism, severe hemorrhagic disorders, or unstable diabetes mellitus. Omegaven™ has been used investigationally in Germany and Taiwan in premature infants as well as term infants as a supplement to conventional fat emulsions.

Monitoring for toxicity due to Omegaven™ was assessed by analyzing clinical and laboratory parameters including serum electrolytes, hematological studies, blood pH, $pCO_2$, and $PO_2$, serum triglycerides, total cholesterol, essential fatty acid profiles, blood and urine glucose and liver and renal function tests (FIG. 6).

Cholestasis is defined as a direct bilirubin greater than 2. This patients direct bilirubin began at 3.3 and has been as high as 3.7. This has dropped, at five weeks of therapy, to 1.7, which is the lowest since one month of age. The total bilirubin declined to 2.5 and is also the lowest since one month of age. C-reactive protein (CRP) is a serum measurement of inflammation and at day 31 has dropped to 0.61 (<0.5 normal) from 1.85. Thus, the treatment regime was sufficient to resolve the patients cholestasis.

REFERENCES

The references cited herein and throughout the specification are incorporated herein by reference.
1. Angulo P 2002 Nonalcoholic fatty liver disease. N Engl J Med 346:1221-1231
2. Clark J M, Brancati F L, Diehl A M 2002 Nonalcoholic fatty liver disease. Gastroenterology 122:1649-1657
3. Clark J M, Diehl A M 2003 Defining nonalcoholic fatty liver disease: implications for epidemiologic studies. Gastroenterology 124:248-250
4. Teli M R, James O F, Burt A D, Bennett M K, Day C P 1995 The natural history of nonalcoholic fatty liver: a follow-up study. Hepatology 22:1714-1719
5. Clark J M, Brancati F L, Diehl A M 2003 The prevalence and etiology of elevated aminotransferase levels in the United States. Am J Gastroenterol 98:960-967
6. Bellentani S, Saccoccio G, Masutti F, Croce L S, Brandi G, Sasso F, Cristanini G, Tiribelli C 2000 Prevalence of and risk factors for hepatic steatosis in Northern Italy. Ann Intern Med 132:112-117
7. Wanless I R, Lentz J S 1990 Fatty liver hepatitis (steatohepatitis) and obesity: an autopsy study with analysis of risk factors. Hepatology 12:1106-1110
8. Ratziu V, Giral P, Charlotte F, Bruckert E, Thibault V, Theodorou I, Khalil L, Turpin G, Opolon P, Poynard T 2000 Liver fibrosis in overweight patients. Gastroenterology 118:1117-1123
9. Ruderman N, Chisholm D, Pi-Sunyer X, Schneider S 1998 The metabolically obese, normal-weight individual revisited. Diabetes 47:699-713
10. Clark J M, Diehl A M 2002 Hepatic steatosis and type 2 diabetes mellitus. Curr Diab Rep 2:210-215
11. Sahoo S, Hart J 2003 Histopathological features of L-asparaginase-induced liver disease. Semin Liver Dis 23:295-299
12. Kooby D A, Fong Y, Suriawinata A, Gonen M, Allen P J, Klimstra D S, DeMatteo R P, D'Angelica M, Blumgart L H, Jarnagin W R 2003 Impact of steatosis on perioperative outcome following hepatic resection. J Gastrointest Surg 7:1034-1044
13. Sax H C, Talamini M A, Brackett K, Fischer J E 1986 Hepatic steatosis in parenteral nutrition: failure of fatty infiltration to correlate with abnormal serum hepatic enzyme levels. Surgery 100:697-704
14. Sax H C, Bower R H 1988 Hepatic complications of parenteral nutrition. JPEN J Parenter Enteral Nutr 12:615-618
15. Hughes C A, Talbot I C, Ducker D A, Harran M J 1983 Parenteral nutrition in infancy: effect on the liver and suggested pathogenesis. Gut 24:241-248
16. Benjamin D R 1981 Hepatobiliary dysfunction in infants and children associated with long-term parenteral nutrition. A clinico-pathologic study. Am J Clin Pathol 76:276-283
17. Mullick F G, Moran C A, Ishak K G 1994 Parenteral nutrition: a histopathologic analysis of the liver changes in 20 children. Mod Pathol 7:190-194
18. Levine A, Maayan A, Shamir R, Dinari G, Sulkes J, Sirotta L 1999 Parenteral nutrition-associated cholestasis in preterm neonates: evaluation of ursodeoxycholic acid treatment. J Pediatr Endocrinol Metab 12:549-553
19. Kaufman S S 2002 Prevention of parenteral nutrition-associated liver disease in children. Pediatr Transplant 6:37-42
20. Day C P, James O F 1998 Steatohepatitis: a tale of two "hits"? Gastroenterology 114:842-845
21. Day C P 2002 Pathogenesis of steatohepatitis. Best Pract Res Clin Gastroenterol 16:663-678
22. Helms R A, Miller J L, Burckart G J, Allen R G 1983 Clinical outcome as assessed by anthropometric parameters, albumin, and cellular immune function in high-risk infants receiving parenteral nutrition. J Pediatr Surg 18:564-569
23. Moss R L, Das J B, Raffensperger J G 1993 Parenteral nutrition-associated cholestasis: clinical and histopathologic correlation. J Pediatr Surg 28:1270-1274; discussion 1274-1275
24. Moss R L, Haynes A L, Pastuszyn A, Glew R H 1999 Methionine infusion reproduces liver injury of parenteral nutrition cholestasis. Pediatr Res 45:664-668
25. Su K P, Huang S Y, Chiu C C, Shen W W 2003 Omega-3 fatty acids in major depressive disorder. A preliminary double-blind, placebo-controlled trial. Eur Neuropsychopharmacol 13:267-271
26. Freeman M P 2000 Omega-3 fatty acids in psychiatry: a review. Ann Clin Psychiatry 12:159-165
27. Arvindakshan M, Ghate M, Ranjekar P K, Evans D R, Mahadik S P 2003 Supplementation with a combination of omega-3 fatty acids and antioxidants (vitamins E and C) improves the outcome of schizophrenia. Schizophr Res 62:195-204
28. Mata Lopez P, Ortega R M 2003 Omega-3 fatty acids in the prevention and control of cardiovascular disease. Eur J Clin Nutr 57:S22-S25
29. Leaf A, Kang J X, Xiao Y F, Billman G E 2003 Clinical prevention of sudden cardiac death by n-3 polyunsaturated fatty acids and mechanism of prevention of arrhythmias by n-3 fish oils. Circulation 107:2646-2652
30. Simopoulos A P 2002 Omega-3 fatty acids in inflammation and autoimmune diseases. J Am Coll Nutr 21:495-505
31. De Vizia B, Raia V, Spano C, Pavlidis C, Coruzzo A, Alessio M 2003 Effect of an 8-month treatment with omega-3 fatty acids (eicosapentaenoic and docosahexaenoic) in patients with cystic fibrosis. JPEN J Parenter Enteral Nutr 27:52-57
32. Chen M F, Lee Y T, Hsu H C, Yeh P C, Liau C S, Huang P C 1992 Effects of dietary supplementation with fish oil on prostanoid metabolism during acute coronary occlusion with or without reperfusion in diet-induced hypercholesterolemic rabbits. Int J Cardiol 36:297-304
33. Novak T E, Babcock T A, Jho D H, Helton W S, Espat N J 2003 NF-kappa B inhibition by omega-3 fatty acids modulates LPS-stimulated macrophage TNF-alpha transcription. Am J Physiol Lung Cell Mol Physiol 284:L84-L89
34. Babcock T A, Novak T, Ong E, Jho D H, Helton W S, Espat N J 2002 Modulation of lipopolysaccharide-stimulated macrophage tumor necrosis factor-alpha production by omega-3 fatty acid is associated with differential cyclooxygenase-2 protein expression and is independent of interleukin-10. J Surg Res 107:135-139 35. Mayer K, Merfels M, Muhly-Reinholz M, Gokorsch S, Rosseau S, Lohmeyer J, Schwarzer N, Krull M, Suttorp N, Grimminger F, Seeger W 2002 Omega-3 fatty acids suppress monocyte adhesion to human endothelial cells: role of endothelial PAF generation. Am J Physiol Heart Circ Physiol 283:H811-H818

36. Mayer K, Meyer S, Reinholz-Muhly M, Maus U, Merfels M, Lohmeyer J, Grimminger F, Seeger W 2003 Short-time infusion of fish oil-based lipid emulsions, approved for parenteral nutrition, reduces monocyte proinflammatory cytokine generation and adhesive interaction with endothelium in humans. J Immunol 171:4837-4843

37. Rallidis L S, Paschos G, Liakos G K, Velissaridou A H, Anastasiadis G, Zampelas A 2003 Dietary alpha-linolenic acid decreases C-reactive protein, serum amyloid A and interleukin-6 in dyslipidaemic patients. Atherosclerosis 167:237-242

38. Park Y, Harris W S 2003 Omega-3 fatty acid supplementation accelerates chylomicron triglyceride clearance. J Lipid Res 44:455-463

39. Van Aerde J E, Duerksen D R, Gramlich L, Meddings J B, Chan G, Thomson A B, Clandinin M T 1999 Intravenous fish oil emulsion attenuates parenteral nutrition-induced cholestasis in newborn piglets. Pediatr Res 45:202-208

40. Yeh S L, Chang K Y, Huang P C, Chen W J 1997 Effects of n-3 and n-6 fatty acids on plasma eicosanoids and liver antioxidant enzymes in rats receiving parenteral nutrition. Nutrition 13:32-36

41. Chen W J, Yeh S L 2003 Effects of fish oil in parenteral nutrition. Nutrition 19:275-279

42. Sekiya M, Yahagi N, Matsuzaka T, Najima Y, Nakakuki M, Nagai R, Ishibashi S, Osuga J, Yamada N, Shimano H 2003 Polyunsaturated fatty acids ameliorate hepatic steatosis in obese mice by SREBP-1 suppression. Hepatology 38:1529-1539

43. Araya J, Rodrigo R, Videla L, Thielemann L, Orellana M, Pettinelli P, Poniachik J 2004 Increase in long-chain polyunsaturated fatty acid n-6/n-3 ratio in relation to hepatic steatosis in non-alcoholic fatty liver disease patients. Clin Sci (Lond) 106:635-643

44. Colomb V, Jobert-Giraud A, Lacaille F, Goulet O, Fournet J C, Ricour C 2000 Role of lipid emulsions in cholestasis associated with long-term parenteral nutrition in children. JPEN J Parenter Enteral Nutr 24:345-350

45. Alwayn I P, Javid P J, Gura K M, Nose V, Ollero M, Puder M 2004 Do polyunsaturated fatty acids ameliorate hepatic steatosis in obese mice by SREPB-1 suppression or by correcting essential fatty acid deficiency. Hepatology 39:1176-1177; author reply 1177-1178

46. Alvarez J G, Touchstone J C 1992 Separation of acidic and neutral lipids by aminopropyl-bonded silica gel column chromatography. J Chromatogr 577:142-145

47. Yang H, Finaly R, Teitelbaum D H 2003 Alteration in epithelial permeability and ion transport in a mouse model of parenteral nutrition. Crit Care Med 31:1118-1125

48. Ohta K, Omura K, Hirano K, Kanehira E, Ishikawa N, Kato Y, Kawakami K, Watanabe G 2003 The effects of an additive small amount of a low residual diet against parenteral nutrition-induced gut mucosal barrier. Am J Surg 185:79-85

49. Reeves P G, Nielsen F H, Fahey G C, Jr. 1993 AIN-93 purified diets for laboratory rodents: final report of the American Institute of Nutrition ad hoc writing committee on the reformulation of the AIN-76A rodent diet. J Nutr 123:1939-1951

50. Keim N L, Mares-Perlman J A 1984 Development of hepatic steatosis and essential fatty acid deficiency in rats with hypercaloric, fat-free parenteral nutrition. J Nutr 114:1807-1815

51. Goheen S C, Larkin E C, Rao G A 1983 Severe fatty liver in rats fed a fat-free ethanol diet, and its prevention by small amounts of dietary arachidonate. Lipids 18:285-290

52. Allardyce D B 1982 Cholestasis caused by lipid emulsions. Surg Gynecol Obstet 154:641-647

53. Cavicchi M, Crenn P, Beau P, Degott C, Boutron M C, Messing B 1998 Severe liver complications associated with long-term parenteral nutrition are dependent on lipid parenteral input. Transplant Proc 30:2547

54. Cavicchi M, Beau P, Crenn P, Degott C, Messing B 2000 Prevalence of liver disease and contributing factors in patients receiving home parenteral nutrition for permanent intestinal failure. Ann Intern Med 132:525-532

55. Clayton P T, Whitfield P, Iyer K 1998 The role of phytosterols in the pathogenesis of liver complications of pediatric parenteral nutrition. Nutrition 14:158-164

56. Chen W J, Yeh S L, Huang P C 1996 Effects of fat emulsions with different fatty acid composition on plasma and hepatic lipids in rats receiving parenteral nutrition. Clinical Nutrition 15:24-28

57. Zaman N, Tam Y K, Jewell L D, Coutts R T 1997 Effects of intravenous lipid as a source of energy in parenteral nutrition associated hepatic dysfunction and lidocaine elimination: a study using isolated rat liver perfusion. Biopharm Drug Dispos 18:803-819

58. Fernandes G 1994 Dietary lipids and risk of autoimmune disease. Clin Immunol Immunopathol 72:193-197

59. Burdge G C, Finnegan Y E, Minihane A M, Williams C M, Wootton S A 2003 Effect of altered dietary n-3 fatty acid intake upon plasma lipid fatty acid composition, conversion of [13C]alpha-linolenic acid to longer-chain fatty acids and partitioning towards beta-oxidation in older men. Br J Nutr 90:311-321

60. Neschen S, Moore 1, Regittnig W, Yu C L, Wang Y, Pypaert M, Petersen K F, Shulman G I 2002 Contrasting effects of fish oil and safflower oil on hepatic peroxisomal and tissue lipid content. Am J Physiol Endocrinol Metab 282:E395-E401

61. Willumsen N, Hexeberg S, Skorve J, Lundquist M, Berge R K 1993 Docosahexaenoic acid shows no triglyceride-lowering effects but increases the peroxisomal fatty acid oxidation in liver of rats. J Lipid Res 34:13-22

62. Rustan A C, Nossen J O, Christiansen E N, Drevon C A 1988 Eicosapentaenoic acid reduces hepatic synthesis and secretion of triacylglycerol by decreasing the activity of acyl-coenzyme A:1,2-diacylglycerol acyltransferase. J Lipid Res 29:1417-1426

63. Nossen J O, Rustan A C, Gloppestad S H, Malbakken S, Drevon C A 1986 Eicosapentaenoic acid inhibits synthesis and secretion of triacylglycerols by cultured rat hepatocytes. Biochim Biophys Acta 879:56-65

64. Bellenger J, Bellenger S, Clement L, Mandard S, Diot C, Poisson J P, Narce M 2004 A new hypotensive polyunsaturated fatty acid dietary combination regulates oleic acid accumulation by suppression of stearoyl CoA desaturase 1 gene expression in the SHR model of genetic hypertension. Faseb J 18:773-775

Although the foregoing invention has been described in some detail by way of illustration and example for the purposes of clarity of understanding, one skilled in the art will easily ascertain that certain changes and modifications may be practiced without departing from the spirit and scope of the appended claims.

We claim:

1. A method for preventing parenteral nutrition associated liver disease (PNALD) in a human patient obtaining nutritional support through total parenteral nutrition (PN) comprising intravenous administration of an effective amount of a lipid emulsion comprising fish oil derived omega-3-fatty acid as the active ingredient to a human patient obtaining long-term nutritional support through parenteral nutrition, wherein the emulsion does not contain phytosterols or plant derived fatty acids, and wherein the patient is not administered phytosterols or plant derived fatty acids.

2. The method of claim 1, wherein the parenteral nutrition associated liver disease is fatty liver disease.

3. The method of claim 1, wherein the fish oil is derived from a source selected from the group consisting of menhaden, herring, mackerel, cod, caplin, tilapia, tuna, sardine, pacific saury, salmon, arctic char and krill.

4. The method of claim 1, wherein the emulsion is prepared using an emulsifying agent selected from the group consisting of egg phosphatidylcholine, egg lecithin, L-a-dipalmitoyl phosphatidylcholine (DPPC), DL-a-dipalmitoyl phosphatidylethanolamine (DPPE), and dioleoyl phosphatidylcholine (DOPC).

5. The method of claim 1, wherein the patient is a newborn.

6. The method of claim 1, wherein the patient is a premature newborn.

7. The method of claim 1, wherein the patient is an infant.

8. The method of claim 1, wherein the patient is a child under the age of 18.

9. The method of claim 1, wherein the patient is a child under the age of 12.

10. The method of claim 1, wherein the patient is an adult receiving long term nutritional support through parenteral nutrition.

11. The method of claim 1, wherein the emulsion is administered until said patient is capable of receiving adequate nutrition from enteral food intake.

12. The method of claim 1, wherein the omega-3-fatty acid is administered at a dose of 0.2 g/kg/day to 3.0 g/kg/day.

13. The method of claim 1, wherein the omega-3-fatty acid is administered at a dose of 0.5 g/kg/day to 1.0 g/kg/day.

14. The method of claim 1, wherein the patient has short-bowel syndrome.

15. The method of claim 7, wherein the infant is less than 2 years old.

16. A method for preventing parenteral nutrition associated liver disease (PNALD) in a human patient less than two years old obtaining nutritional support solely through parenteral nutrition (PN), the method comprising intravenous administration of an effective amount of a lipid emulsion comprising fish oil derived omega-3-fatty acid as the active ingredient to a human patient less than two years old obtaining long-term nutritional support through parenteral nutrition, wherein the emulsion does not contain phytosterols or plant derived fatty acids, wherein the patient is not administered phytosterols or plant derived fatty acids, and wherein the human patient less than two years old has short-bowel syndrome.

17. The method of claim 1, wherein the administration of the lipid emulsion is for a period greater than 3 weeks.

18. The method of claim 1, wherein the administration of the lipid emulsion is for a period greater than 6 weeks.

19. The method of claim 1, wherein the administration of the lipid emulsion is for a period greater than 3 months.

* * * * *